(12) United States Patent
Boeve et al.

(10) Patent No.: US 8,354,841 B2
(45) Date of Patent: Jan. 15, 2013

(54) METHOD FOR INFLUENCING AND/OR DETECTING MAGNETIC PARTICLES IN A REGION OF ACTION, MAGNETIC PARTICLES AND THE USE OF MAGNETIC PARTICLES

(75) Inventors: Hans Marc Bert Boeve, Hechtel-Eksel (BE); Denis Markov, Veldhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 412 days.

(21) Appl. No.: 12/523,548

(22) PCT Filed: Jan. 18, 2008

(86) PCT No.: PCT/IB2008/050186
§ 371 (c)(1),
(2), (4) Date: Dec. 18, 2009

(87) PCT Pub. No.: WO2008/090500
PCT Pub. Date: Jul. 31, 2008

(65) Prior Publication Data
US 2010/0123456 A1  May 20, 2010

(30) Foreign Application Priority Data
Jan. 24, 2007 (EP) ..................... 07101071

(51) Int. Cl.
G01N 27/72 (2006.01)
(52) U.S. Cl. ........... 324/228; 324/204; 600/12; 128/899
(58) Field of Classification Search ................. 324/228, 324/204; 252/62.51 R; 427/212; 423/633; 600/12; 128/899
See application file for complete search history.

(56) References Cited

U.S. PATENT DOCUMENTS 6,962,685 B2  11/2005  Sun
(Continued)

FOREIGN PATENT DOCUMENTS

DE  10151778 A1  5/2003
(Continued)

OTHER PUBLICATIONS

Zeng et al: "Bimagnetic Core/Shell FePt/Fe3O4 Nanoparticles"; Nano Letters, 2004, vol. 4, No. 1, pp. 187-190.
(Continued)

*Primary Examiner* — Arleen M Vazquez

(57) ABSTRACT

A method for influencing and/or detecting magnetic particles in a region of action, magnetic particles and the use of magnetic particles is disclosed, which method comprises the steps of: —introducing magnetic particles into a region of action, —generating a magnetic selection field having a pattern in space of its magnetic field strength such that a first sub-zone having a low magnetic field strength and a second sub-zone having a higher magnetic field strength are formed in the region of action —changing the position in space of the two sub-zones in the region of action by means of a magnetic drive field so that the magnetization of the magnetic particles change locally, —acquiring signals, which signals depend on the magnetization in the region of action, which magnetization is influenced by the change in the position in space of the first and second sub-zone, wherein the magnetic particles comprise a core region and a shell region, the core region comprising a magnetic material, wherein the magnetic material of the core region is provided as a mainly metallic material of comparably high saturation magnetization, wherein the shell region comprises mainly a metal oxide material or a noble metal material.

13 Claims, 2 Drawing Sheets

U.S. PATENT DOCUMENTS

| | | | |
|---|---|---|---|
| 2001/0012915 A1* | 8/2001 | Avrin et al. | 600/424 |
| 2006/0141149 A1 | 6/2006 | Chen et al. | |
| 2006/0211941 A1* | 9/2006 | Gleich | 600/425 |
| 2006/0228551 A1* | 10/2006 | Chen et al. | 428/402 |
| 2006/0238194 A1 | 10/2006 | Gleich | |
| 2007/0007486 A1* | 1/2007 | Gleich et al. | 252/62.58 |
| 2008/0014442 A1* | 1/2008 | Rida | 428/403 |

FOREIGN PATENT DOCUMENTS

| | | |
|---|---|---|
| EP | 2006064392 A2 | 6/2006 |
| EP | 1710811 A2 | 10/2006 |
| EP | 1738773 A1 | 1/2007 |
| WO | 2004091395 A2 | 10/2004 |
| WO | 2006056579 A2 | 6/2006 |
| WO | 2007002732 A1 | 1/2007 |

OTHER PUBLICATIONS

Ravel et al: "Oxidation of Iron in Iron/Gold Core/Shell Nanoparticles"; Journal of Applied Physics, May 15, 2002, vol. 91, No. 10, pp. M8195-M8197.

Gangopadhyay et al: "Magnetic Properties of Ultrafine Iron Particles"; Physical Revew B, May 1, 2002, vol. 45, No. 17, pp. 9778-9787.

Gijs, M.:"Magnetic Bead Handling On-Chip: New Opportunites for Analytical Applications"; Microfluid Nanofluid (2004), 1, pp. 22-40.

Sun et al: "Effect of Au Coating on the Magnetic and Structural Properties of Fe Nanoclusters for Use in Biomedical Applications: A Density-Functional Theory Study"; Physical Review B, 2006, vol. 73, pp. 134409-1-134409-6.

Kuhn, L. Theil et al "Structural and Magnetic Properties of Core-Shell Iron-Iron Oxide Nanoparticles", Journal of Physics Condensed Matter, vol. 14, 2002, pp. 13551-13567.

Ban, Zhijui "The Synthesys of Core-Shell Iron@Gold Nanoparticles and their Characterization", University of New Orleans Theses and Dissertations, May 21, 2004.

Antony, Jiji et al "Synthesis and Characterization of Stable Iron-Iron Oxide Core-Shell Nanoclusters for Environmental Applications" Journal of Nanoscience and Nanotechnology, vol. 6, No. 6, pp. 568-572, 2006.

Bai, Jianmin et al "High-Magnetic-Moment Core-Shell-Type FeCo-Au/Ag Nanoparticles" Applied Physics Letters, vol. 87, No. 152502, 2005.

Qiang, You et al "Synthesis of Core-Shell Nanoclusters with High Magnetic Moment for Biomedical Applicaitons" IEEE Transactions of Magnetics, vol. 40, No. 6, Nov. 2004, pp. 3538-3540.

* cited by examiner

METHOD FOR INFLUENCING AND/OR DETECTING MAGNETIC PARTICLES IN A REGION OF ACTION, MAGNETIC PARTICLES AND THE USE OF MAGNETIC PARTICLES

The present invention relates to a method for influencing and/or detecting magnetic particles. Furthermore, the invention relates to magnetic particles and to the use of magnetic particles.

A method of such a kind (magnetic particle imaging) is known from German Patent Application DE 101 51 778 A1. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such a method has the advantage that it can be used to examine arbitrary examination objects—e.g. human bodies—in a non-destructive manner and without causing any damage and with a high spatial resolution, both close to the surface and remote from the surface of the examination object.

The performance of such a known method depends strongly on the performance of the tracer material, i.e. the material containing the magnetic particles and therefore it exists the need for magnetic particles that are more suitable for magnetic particle imaging and giving rise to an enhanced signal-to-noise ratio.

It is therefore an object of the present invention to provide a method and magnetic particles in order to provide an enhanced detection and spatial resolution performance.

The above object is achieved by a method for influencing and/or detecting magnetic particles in a region of action, wherein the method comprises the steps of introducing magnetic particles into a region of action, furthermore generating a magnetic selection field having a pattern in space of its magnetic field strength such that a first sub-zone having a low magnetic field strength and a second sub-zone having a higher magnetic field strength are formed in the region of action, furthermore changing the position in space of the two sub-zones in the region of action by means of a magnetic drive field so that the magnetization of the magnetic particles change locally, furthermore acquiring signals, which signals depend on the magnetization in the region of action, which magnetization is influenced by the change in the position in space of the first and second sub-zone, wherein the magnetic particles comprise a core region and a shell region, the core region comprising a magnetic material, wherein the magnetic material of the core region is provided as a mainly metallic material of comparably high saturation magnetization, wherein the shell region comprises mainly a metal oxide material and/or a noble metal material.

The above mentioned object is also achieved by magnetic particles comprising a core region and a shell region, the core region comprising a magnetic material, wherein the magnetic material of the core region is provided as a mainly metallic material of comparably high saturation magnetization, wherein the shell region comprises mainly a metal oxide material and/or a noble metal material.

The advantage of such a method and such magnetic particles is that it is possible to achieve a higher signal-to-noise ratio due to an increased performance of the magnetic particles adapted to the method of magnetic particle imaging. The comparably high saturation magnetization of the core region preferably of at least about 100 emu/g (100 Am$^2$/kg), very preferably of at least about 120 emu/g (120 Am$^2$/kg), most preferably of at least about 150 emu/g (150 Am$^2$/kg) (i.e. higher compared to the saturation magnetization of conventionally used iron oxides as magnetic material of the core region of magnetic core-shell particles) provides the possibility to advantageously reduce the particle size such that a higher range of applications, especially inside a human or animal body (e.g. the intrusion of such small particles inside small body vessels or ducts or in-between body cells) is possible. Furthermore, according to a preferred embodiment of the present invention, the magnetic particles are provided as mono domain magnetic particles. Thereby, it is possible to provide the magnetic particles having a relatively small size of the core region, e.g. 5 nm to 100 nm, preferably 10 nm to 40 nm.

According to a furthermore preferred embodiment of the present invention, the magnetic material of the core region has an anisotropy field of the magnetization, especially in the range of about 1 mT to about 10 mT, preferably about 3 mT to about 5 mT. Thereby, it is advantageously possible to tune the behavior of the magnetic particles such that a high signal to noise ratio is achievable in respect of such inventive magnetic particles compared to magnetic particles having a smaller or a greater anisotropy of their magnetization. In the context of the present invention, the term "strength of anisotropy of the magnetization of magnetic particles" signifies the exterior magnetic field (exterior relative to the magnetic particle or particles) that is necessary in order to change significantly the magnetization of the magnetic particle or particles. This interpretation is strongly correlated to other definitions relatable to the term "anisotropy of magnetic particles" or "field of anisotropy", e.g. different energies related to different spatial directions (energy landscape) expressed by means of a plurality of constants of anisotropy. In the context of the present invention, the term "strength of anisotropy of the magnetization of magnetic particles" is related to a quantifiable parameter. The anisotropy of the magnetization can be due to shape anisotropy and/or crystal anisotropy and/or induced anisotropy and/or surface anisotropy. Thereby, a large choice of possible shapes and/or materials for the magnetic particles is available when using such magnetic particles in accordance with the present invention. Especially with such particles, it is possible to enhance the signal to noise ratio in the application of magnetic particle imaging provided that the external magnetic field that is experienced by the particles is oriented in a specific range of angles relative to the direction of the easy magnetization (easy axis) of the magnetic particles. Generally according to the present invention, i.e. in the context of magnetic particle imaging, it is preferred to use larger particles as they potentially have a larger possible magnetization which in turn can lead to a higher signal-to-noise ratio at the detection stage. Nevertheless, the size of the magnetic particles is limited because larger particles attract each other due to their magnetic moment and form clusters of magnetic particles having a tendency to be invisible or at least less visible to the method of magnetic particle imaging. According to the present invention, small particles of preferably well defined anisotropy of their magnetization are suggested which behave like larger magnetic particles of a different magnetic material in the core region.

Furthermore, it is preferred according to the present invention that the magnetic particles have a specified anisotropy of the magnetization in the range of about 1 mT to about 10 mT, wherein the standard deviation of the anisotropy of their magnetization is less than 1 mT, preferably less than 0.5 mT, most preferably less than 0.25 mT. Thereby, it is advantageously possible by means of the inventive magnetic particles to provide a strong signal because all or at least an important proportion of the magnetic particles behave in a similar and advantageous way.

In a further embodiment of the present invention, it is preferred that the shell region comprises mainly an iron oxide material, preferably a ferrite material, very preferably a magnetite material ($Fe_3O_4$) or a maghemite material ($\gamma$-$Fe_2O_3$) and/or that the shell region comprises mainly a metallic Gold material or metallic Silver material. Thereby, it is possible to use the inventive magnetic particles in medical applications as the level of toxicity can be reduced and the probability of oxidation and/or dissolution can be reduced by providing the shell region.

According to a preferred embodiment of the present invention, the magnetic particles further comprise a coating region at least partly enclosing the shell region such that the coating region is adapted to the environment of the magnetic particles. In the context of the present invention, by the term "environment of the magnetic particles", the environment of the magnetic particles in the desired application is understood, i.e. for example inside the blood and/or another body liquid of a human or animal body or the like. In one alternative embodiment of the coating region, the coating is pharmaceutically removable in the sense that the magnetic particle can be shielded from the environment so that life threatening side effects known in the field do not occur. This is e.g. the case where high concentrations of magnetic particles can be found—for example at the location of injecting the tracer material into the body of patient. In a further alternative embodiment, the coating is biocompatible, i.e. biodegradable and/or biostable, so that particle cluster formation is prevented by a combination of different forces including electrostatic repulsion from ionic charges in the coating or steric hindrance. As a result, colloidal stability can be sustained during tracer material fabrication, storage and use. In a further alternative embodiment, it is advantageously possible to achieve information on the environment of the magnetic particles. Especially, it is, e.g., possible to provide the coating region such that the coating region removes from the particle if a predefined temperature in the environment of the magnetic particles is exceeded. Furthermore, it is possible to provide the coating region such that viscosity measurements are possible in the environment of the magnetic particles. These alternative embodiments of the coating region can also be provided cumulatively or at least partly cumulatively. For further examples of alternative embodiments of the coating region, EP 1738 773 A1 is incorporated by reference in its entirety, especially paragraphs 0009 to 0011.

Furthermore, it is preferred according to the present invention that the coating region comprises at least one targeting ligand reactive to a target molecule or to a plurality of target molecules in an examination area and preferably that the magnetic particles have a reduced rotational mobility after binding to the target molecule or target molecules, wherein the at least one targeting ligand is preferably a biological entity, especially an amino acid or polypeptide or a nucleic acid, and wherein the target molecule is preferably a biological entity, especially an enzyme or a nucleic acid or an antibody. Thereby, it is advantageously possible to specifically adapt the magnetic particles to the information that is to be extracted from the environment of the magnetic particles.

The invention further relates to the use of magnetic particles for magnetic particle imaging, i.e. especially in an above mentioned method.

The magnetic field strength mentioned in the context of the present invention can also be specified in Tesla. This is not correct, as Tesla is the unit of the magnetic flux density. In order to obtain the particular magnetic field strength, the value specified in each case still has to be divided by the magnetic field constant $\mu_0$.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

Figure 4A:
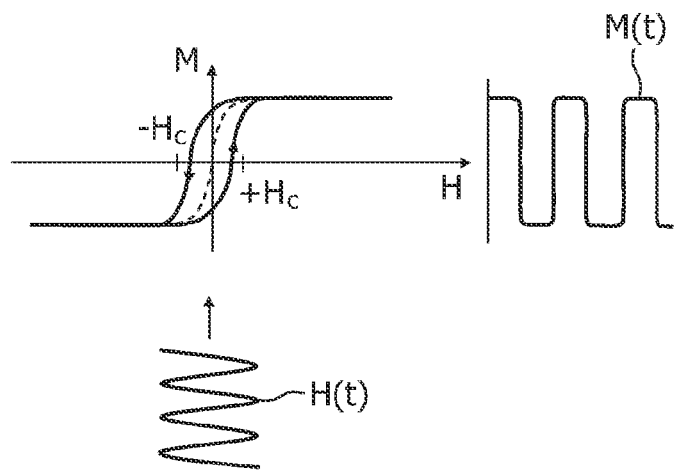
Figure 4B:
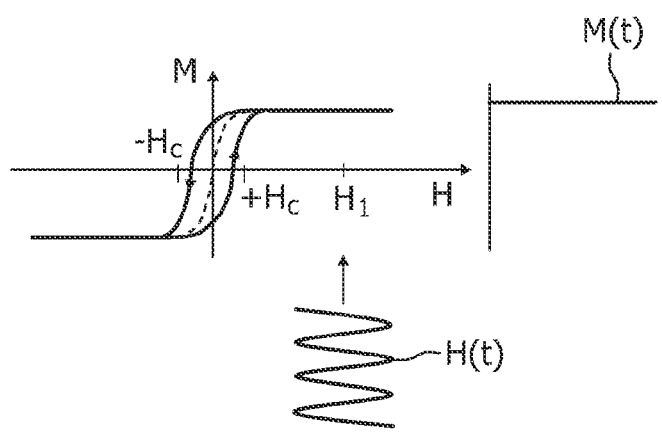

FIGS. 4*a* and 4*b* illustrate the magnetization characteristics of such particles The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1:
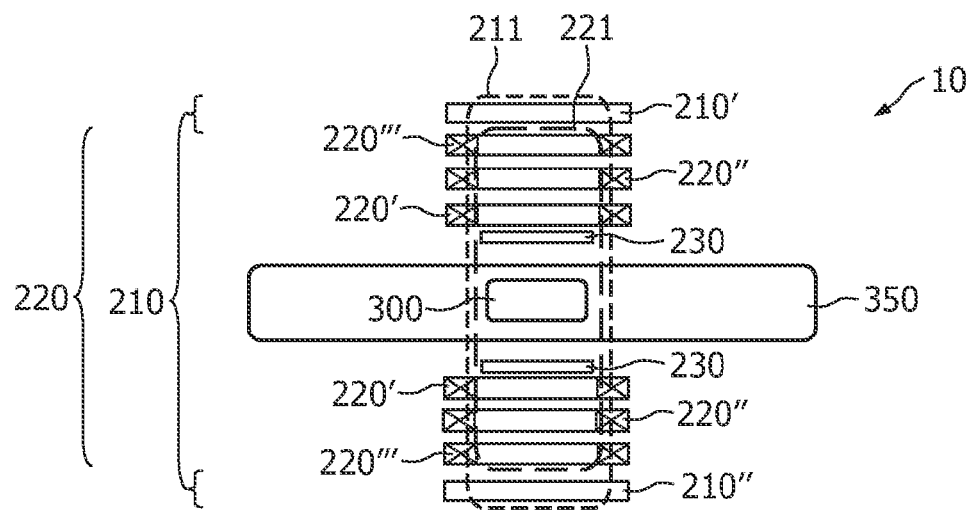
FIG. 1 illustrates an arrangement for carrying out the method according to the present invention.

In FIG. 1, an arbitrary object to be examined by means of an arrangement 10 for carrying out the method according to the present invention is shown. The reference numeral 350 in FIG. 1 denotes an object, in this case a human or animal patient, who is arranged on a patient table, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350 or which is swallowed by the patient 350.

Figure 2:
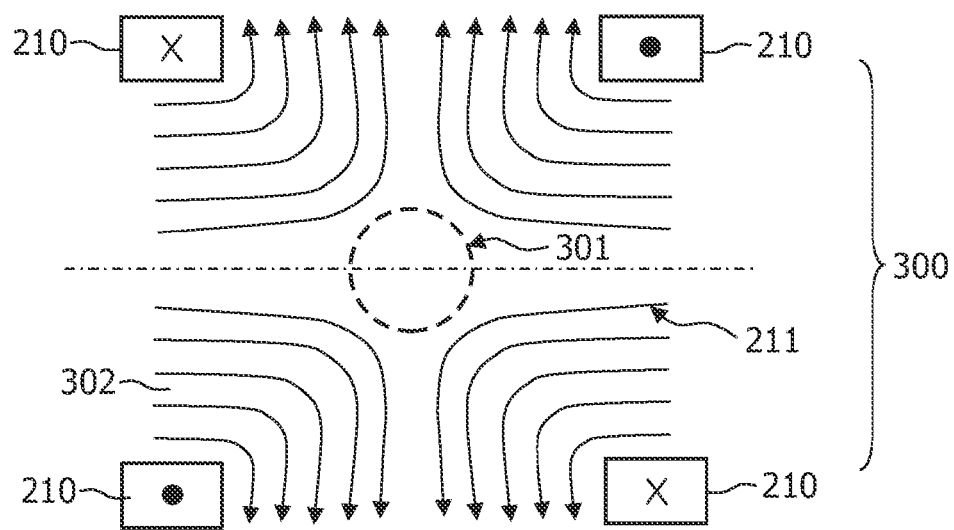
FIG. 2 illustrates an example of the field line pattern produced by such an arrangement.

The arrangement 10 comprises a plurality of coils forming a selection means 210 whose range defines the region of action 300 which is also called the region of examination 300. For example, the selection means 210 comprise a first pair of coils 210', 210". The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point, the field strength is so small that the magnetization of the magnetic particles 100 present in that first sub-zone 301 is not saturated, whereas the magnetization of the magnetic particles 100 present in a second sub-zone 302 (outside the region 301) is in a state of saturation. In the second sub-zone 302 (i.e. in the residual part of the region of action 300 outside of the first sub-zone 301) the magnetic field strength is sufficiently strong to keep the magnetic particles 100 in a state of saturation. By changing the position of the two sub-zones 301, 302 within the region of action 300, the (overall) magnetization in the region of action 300 changes. By measuring the magnetization in the region of action 300 or a physical parameter influenced by the magnetization, information about the spatial distribution of the magnetic particles 100 and/or about the physical, chemical or biological environment of the magnetic particles in the region of action can be obtained.

When a further magnetic field—in the following called a magnetic drive field 221 (FIG. 1)—is superposed on the magnetic selection field 210 (or gradient magnetic field 210) in the region of action 300, the first sub-zone 301 is shifted relative to the second sub-zone 302. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics, i.e. the due to saturation effects. In order to generate the magnetic drive field 221 for any given direction in space, there are provided, e.g., three drive coil pairs, namely a first drive coil pair 220', a second drive coil pair 220" and a third drive coil pair 220''' which together are called drive means 220 in the following. The components of the magnetic drive field 221 due to the drive coil pairs 220', 220", 220''' can vary, e.g. in their direction. The arrangement 10 further comprise receiving means 230 that are only schematically shown in FIG. 1. The receiving means 230 usually comprise coils that are able to detect the signals induced by the magnetization pattern of the magnetic particle 100 in the region of action 300. Such an arrangement and such a method of detecting magnetic particles are known from DE 101 51 778 which is hereby incorporated in its entirety.

Figure 3:
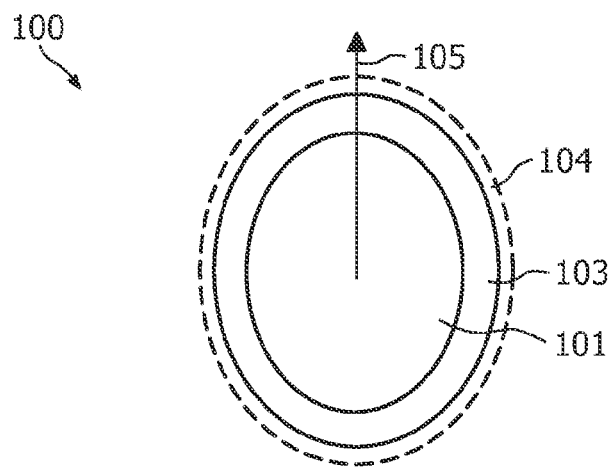
FIG. 3 illustrates an enlarged view of a magnetic particle present in the region of action.

FIG. 3 shows schematically an example of a magnetic particle 100 of the present invention used together with the method according to the present invention.

The magnetic particles 100 comprise a mono domain magnetic material 101 that also constitutes a core region 101 of the magnetic particles 100. The magnetic material in the core region 101 is provided, e.g., of the ferromagnetic type and has a comparably high saturation magnetization. According to the present invention, a metallic material (or a hard magnetic material) having a comparably high saturation magnetization is used as the magnetic material in the core region 101 of the magnetic particles 100. Examples of such magnetic materials include the following:

so-called bcc-iron (bcc-Fe) having a saturation magnetization of about 220 emu/g, so-called fcc-cobalt (fcc-Co) having a saturation magnetization of about 170 emu/g, $Fe_{50}Co_{50}$ having a saturation magnetization of about 240 emu/g, other alloys of Ni, Fe, and Co, further including alloys with non-magnetic elements such as Mn, Cu, Cr, Pt, Ba, Gd, Ho, Sm, etc., e.g. FePt alloys.

By using such materials, the signal to noise ratio can be enhanced due to the higher magnetic moment per unit of volume. Therefore, the size of the core region 101 of the magnetic particle 100 and therefore also the overall size of the magnetic particle 100 can advantageously be reduced according to the present invention. This provides a way to tune the dynamic response of the magnetic particles 100, i.e. showing either a Néel behaviour or a Brownian behaviour.

The magnetic field strength of the magnetic selection field 211 required for the saturation of the magnetization of such particles 100 is dependent on various parameters, e.g. the diameter of the particles 100, the used magnetic material 101 and other parameters. It is preferred according to the present invention that the magnetic particles 100 are magnetically anisotropic (denoted by an oval shape of the magnetic particle 100), i.e. they have an anisotropy of their magnetization. Such an anisotropy can e.g. be provided by means of shape anisotropy and/or by means of crystal anisotropy and/or by means of induced anisotropy and/or by means of surface anisotropy. The magnetic particle 100 comprises a direction of easy magnetization, also called easy axis 105. The magnetic drive field 220 produces at the location of the first sub-zone 301 a magnetic drive vector corresponding to the direction of the external magnetic field that the magnetic particle 100 experiences.

If mono domain magnetic particles having an anisotropy of their magnetization are exposed to an external magnetic field, the response of the magnetic particles depends on the direction of the field with respect to the direction of easy magnetization (easy axis). In the example shown in FIG. 3, the anisotropy of the magnetic particle 100 is provided by means of shape anisotropy of the core region 101 of the magnetic particles 100.

According to the present invention, the magnetic material of the core region 101 is covered by means of a material in a shell region 103 which protects the magnetic material 101 of the core region 101 against chemically and/or physically aggressive environments, e.g. acids or oxidising agents (e.g. in the blood or in the stomach). As examples for a material in the shell region 103, iron oxides and/or noble (inert) metals are given. These materials of the shell region 103 can be provided covering the magnetic material of the core region 101. Thereby, one single layer of mainly uniform material is possible. Alternatively, different layers inside the shell region 103 are possible (not depicted in FIG. 3). Examples of inert (noble) metals include gold (Au) and/or silver (Ag).

According to a preferred embodiment of the present invention, the magnetic particles 100 also comprise a coating region 104 that at least partially encloses the shell region 103 of the magnetic particle 100. The coating region 104 is especially provided in order to provide a defined interaction of the magnetic particles 100 with their environment, e.g. by means of influencing the rotational and/or translational mobility of the magnetic particles 100. Especially, it is possible to provide one functional group or a plurality of functional groups reactive to a target molecule or reactive to a plurality of target molecules. The binding of the functional group to the target molecule can be used i.e. in order to reduce the rotational and/or translational mobility of the magnetic particles 100. The functional group can be selected from biological entities like: amino acid or amino acids, polypeptides, nucleic acids. The target molecule can be selected from biological entities like: enzymes, nucleic acids, antibodies or the like.

FIGS. 4a and 4b show the magnetization characteristic, that is, the variation of the magnetization M of a part of the magnetic particles 100 (not shown in FIGS. 4a and 4b) as a function of the field strength H at the location of that part of the magnetic particle 100. It appears that the magnetization M no longer changes beyond a field strength $+H_c$ and below a field strength $-H_c$, which means that a saturated magnetization is involved. The magnetization M is not saturated between the values $+H_c$ and $-H_c$.

FIG. 4a illustrates the effect of a sinusoidal magnetic field H(t) on a part of the magnetic particles 100 where the absolute values of the resulting sinusoidal magnetic field H(t) (i.e. "seen by the magnetic particles 100") are lower than the magnetic field strength required to saturate the magnetic particles 100, i.e. in the case where no further magnetic field is active. The magnetization of the magnetic particles 100 reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of the magnetic particles 100 is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$.

FIG. 4b shows the effect of a sinusoidal magnetic field H(t) on which a further magnetic field $H_1$ (having a frequency that is small relative to the frequency of the sinusoidal magnetic field H(t)) is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

The invention claimed is:

1. A method of influencing and detecting magnetic particles in a region of action the method comprising acts of:
   introducing the magnetic particles into the region of action, the magnetic particles including a shell region and a core region having a comparably high saturation magnetization;
   generating a magnetic selection field including a first sub-zone having a low magnetic field strength and a second sub-zone having a higher magnetic field strength in the region of action;
   superimposing a magnetic drive field on the magnetic selection field for changing the position in space of the first and second sub-zones in the region of action for changing magnetization of the magnetic particles; and
   acquiring signals dependent on the magnetization in the region of action, the magnetization is influenced by the change in the position in space of the first and second sub-zone, the signals from the magnetic particles in the first sub-zone are acquired in a higher frequency band than the magnetic drive field.

2. The method according to claim 1, wherein the core region comprising a magnetic material, the magnetic material of the core region is provided as a mainly metallic material of comparably high saturation magnetization, the shell region comprises mainly a metal oxide material and/or a noble metal material.

3. The method according to claim 2, wherein the magnetic material of the core region has a saturation magnetization selected from one of at least about 100 emu/g (Am$^2$/kg), at least about 120 emu/g (Am$^2$/kg), and at least about 150 emu/g (Am$^2$/kg).

4. The method according to claim 2, wherein the magnetic material of the core region has an anisotropy of the magnetization.

5. The method according to claim 4, wherein the anisotropy of the magnetization is provided in the range selected from one of about 1 mT to about 10 mT, and about 3 mT to about 5 mT.

6. The method according to claim 4, wherein the magnetic particles are having a specified anisotropy of the magnetization in the range of about 1 mT to about 10 mT, the standard deviation of the anisotropy of the magnetization is selected from one of less than 1 mT, less than 0.5 mT, and less than 0.25 mT.

7. The method according to claim 2, wherein the shell region is selected from one of mainly an iron oxide material, a ferrite material, a magnetite material ($Fe_3O_4$), or a maghemite material ($\gamma$-$Fe_2O_3$).

8. The method according to claim 2, wherein the shell region is selected from one of mainly a metallic Gold material or metallic Silver material.

9. The method according to claim 1, wherein the magnetic particles are provided as mono domain magnetic particles.

10. The method according to claim 1, wherein the magnetic particles further comprise a coating region at least partly enclosing the shell region such that the coating region is adapted to the environment of the magnetic particles.

11. The method according to claim 10, wherein the coating region comprises at least one targeting ligand reactive to a target molecule or to a plurality of target molecules in an examination area.

12. The method according to claim 11, wherein the magnetic particles have a reduced rotational mobility after binding to the target molecule or target molecules, wherein the at least one targeting ligand is preferably a biological entity, especially an amino acid or polypeptide or a nucleic acid, and wherein the target molecule is preferably a biological entity, especially an enzyme or a nucleic acid or an antibody.

13. The method according to claim 1, wherein the particles are used for magnetic particle imaging.

* * * * *